United States Patent
Johansson et al.

(10) Patent No.: US 8,152,811 B2
(45) Date of Patent: Apr. 10, 2012

(54) POSITIONING DEVICE FOR A PROSTHESIS DEVICE AND SYSTEM THEREFORE

(75) Inventors: Erik Johansson, Uppsala (SE); Niklas Axen, Järlasa (SE); Staffan Bowald, Fjärdhundra (SE); Sven Olerud, Länna (SE); Hans Jacobsen, Täby (SE)

(73) Assignee: OrtoWay AB, Djursholm (SE)

( * ) Notice: Subject to any disclaimer, the term of this patent is extended or adjusted under 35 U.S.C. 154(b) by 669 days.

(21) Appl. No.: 11/921,365

(22) PCT Filed: May 31, 2006

(86) PCT No.: PCT/SE2006/000642
§ 371 (c)(1),
(2), (4) Date: Mar. 12, 2009

(87) PCT Pub. No.: WO2006/130085
PCT Pub. Date: Dec. 7, 2006

(65) Prior Publication Data
US 2009/0216239 A1 Aug. 27, 2009

(30) Foreign Application Priority Data
Jun. 1, 2005 (SE) .................................... 0501253

(51) Int. Cl.
*A61B 17/70* (2006.01)
(52) U.S. Cl. .................................................. 606/86 A
(58) Field of Classification Search ............ 606/99–100, 606/86 A, 914
See application file for complete search history.

(56) References Cited

U.S. PATENT DOCUMENTS

| | | | |
|---|---|---|---|
| 4,997,432 | A | 3/1991 | Keller |
| 6,174,311 | B1 | 1/2001 | Branch et al. |
| 2004/0158327 | A1 | 8/2004 | Bagby |
| 2004/0193271 | A1 | 9/2004 | Fraser et al. |
| 2004/0225295 | A1 | 11/2004 | Zubok et al. |
| 2005/0027300 | A1 | 2/2005 | Hawkins et al. |
| 2005/0075643 | A1 | 4/2005 | Schwab et al. |

FOREIGN PATENT DOCUMENTS

| | | |
|---|---|---|
| DE | 101 49 385 A1 | 4/2003 |
| WO | WO 02/071986 A2 | 9/2002 |
| WO | WO 03/071992 A2 | 9/2003 |

OTHER PUBLICATIONS

International Search Report, PCT Application No. PCT/SE2006/000642, date of mailing Sep. 11, 2006 and Written Opinion of the International Searching Authority.

*Primary Examiner* — Thomas C. Barrett
*Assistant Examiner* — Sameh Boles
(74) *Attorney, Agent, or Firm* — Mintz Levin Cohn Ferris Glovsky and Popeo, P.C.

(57) ABSTRACT

A positioning device for placing a prosthesis device in a spinal column of a living mammal, the device including at least one holding means for cooperation with the prosthesis device and for guiding thereof during positioning. The positioning device may also include fixing means for fixation with respect to at least one vertebra, where the fixing means includes locking means, which in a first, free state, allows adjustable movement of the holding device and thereby of the prosthesis device, and in a second, locked state, fixes the holding means and thereby the prosthesis device in a selected position. Embodiments of the disclosure also include Embodiments of the invention also include a system.

22 Claims, 4 Drawing Sheets

POSITIONING DEVICE FOR A PROSTHESIS DEVICE AND SYSTEM THEREFORE

CROSS REFERENCE TO RELATED APPLICATIONS

This application is a national stage entry of PCT/SE2006/000642, having an international filing date of May 31, 2006, which claims priority to Swedish patent application no. SE 0501253-9, filed Jun. 1, 2005. Each of the foregoing disclosures is expressly incorporated herein in its entirety.

FIELD OF THE INVENTION

The invention concerns a positioning device and a system for engagement with vertebrae in a spinal column including such a positioning device.

BACKGROUND OF THE INVENTION

For patients diagnosed with disc degeneration, surgical operations are performed more and more often. The most common operation for these patients today is fusion, where an ossified connection of vertebrae is obtained. Also, metallic connection devices can be used. Movability then ceases between the vertebrae in question but the patient will become free from pain. As the patient becomes more active and movable, the segments above and below the fused region will, however, be subjected to greater strains. The risk of new symptoms from surrounding segments thereby increases.

As an alternative to fusion, disc implants have been presented. A known disc prosthesis generally consists of two mutually articulated plates that are positioned between two vertebrae instead of the disc. The positioning of a disc implant results in eliminating the disc that causes pain, reinstating the distance between the vertebrae and reinstating movability between them.

In order to obtain sufficient certainty against a disc implant moving, over time, in an undesired manner from the intended position between two vertebrae, two mutually articulated plates of a previously known prosthesis are provided with different kinds of projecting engagement means, such as fin-shaped elements, pointed elements, pins and like plural projections for the engagement with the meeting surfaces of the vertebrae.

An operative method that is used for inserting a disc implant requires positioning of the prosthesis from the abdomen side in order to allow access to the vertebral column from the front. The disc to be replaced is cleared out, whereby the vertebrae are drawn apart with the aid of tension pliers.

After using instruments for shaping grooves in the surfaces of vertebrae for the cooperation with possible projecting protrusions for the purpose of achieving a correct position for the disc prosthesis, the latter is now to be positioned.

According to today's methods, this is achieved by placing the prosthesis on a holder and hammering it in with great force between the vertebrae, guided by the prepared grooves. This step in the operation is very problematic, since the vertebrae tend to be drawn against each other and then it is often difficult to implant the prosthesis between the vertebrae. For this reason, implantation by hammering is risky.

When the prosthesis is finally positioned, which is verified with X-ray radioscopy, tension pliers are used in order to again span apart the vertebrae, and thereby the disc plates of the prosthesis, in order to be able to position a joint detail between these plates. Also this step is troublesome and sometimes laborious.

When using prostheses that are completely assembled which include the joint detail, this second step is not necessary. Such prostheses are, however, thicker and thus, more troublesome to position between the vertebrae. Sometimes, unfortunately, damage to the vertebrae can occur during the positioning of the prosthesis. Such damage can be serious and have serious consequences. For that reason, the surgical operation puts great demands on the skill and experience of the surgeon.

When, finally, everything is place, the operation is terminated and a final X-ray is made. Sometimes, it is discovered that the disc prosthesis is positioned in such a way that it is not placed exactly on the middle line or is not in a proper position. The possibilities of adjusting the position are at this stage almost none.

Since the disc prosthesis rests on the brittle covering plate of the vertebra, the prosthesis must have maximal size in order to support on a relatively strong peripheral rim of the vertebra. Exact positioning is therefore very essential. Patient having osteoporosis are therefore often disqualified for this type of surgical operation depending on lack of congruence between the parts of the disc prosthesis and the vertebra.

Incorrect positioning results in risk of uncontrolled separation and repositioning of the vertebrae.

OBJECTS AND IMPORTANT FEATURES OF THE INVENTION

It is an aim of the present invention to provide a positioning device of the kind mentioned initially and a system which makes it possible to eliminate or at least reduce the problems of the background art.

These aims and advantage of the present invention can be achieved in a positioning device according to features disclosed herein.

Hereby it is achieved that when two vertebrae of the vertebrae in a spinal column are push apart, a prosthesis device, such as for example a disc prosthesis or a vertebral prosthesis, can be correctly positioned with respect to at least one vertebra when the vertebrae are spanned, e.g., pushed, apart, so that, when the separation is ended, the prosthesis is indeed in the right position. X-ray radioscopy can be used in connection with adjusting holding means of the disclosed embodiments in order to assist the surgeon during the positioning. The invention is, however, not limited to this method, but also other corresponding methods for this are possible to use, such as for example translucence with NMR-camera, magnet camera. Also, other fluoroscopy and positioning indication methods can be used.

When the pushed apart vertebrae are released against the prosthesis device, through X-ray radioscopy or the like, the final position of the prosthesis device can be verified that it is in the desired position. In the event this is not the case, there is a real possibility of repositioning the prosthesis device after a renewed pushing apart of the vertebrae, although this would not be necessary if the positioning is made accurately from the beginning.

After a verified correct positioning, the holding device is released from the prosthesis device, whereafter the used device can be removed permanently. Altogether, the positioning device according to the invention allows essentially more secure and further, more easily handled equipment, which also can be used in a patient-friendly manner with minimized risks of injuries to the patient when it is used.

By providing two fixing elements for different engagement positions and which are mutually lockable, satisfactory stability is obtained and positioning security after possibility of adjustment.

By providing a universal joint, which is lockable/releasable through locking means, great positioning freedom is provided.

In particular, it is preferred that the positioning device according to the invention includes distance means having connection portions which carry engagement means that are constructed for engagement with two vertebrae at a distance from each other. Hereby the prosthesis device is positioned with respect to these vertebrae, which are preferably located on either side of the operation point.

In particular, it is preferred that the distance means are arranged such that they are capable of changing the degree of separation of the vertebrae when the engagement means are in engagement therewith. Hereby, in the positioning device, the means for spanning apart the vertebrae are integrated which is a considerable advantage since the arrangement for spanning apart can be constructed optimally to function as a mechanism for spanning apart, and further, as the base for the fixing means. Greater freedom when removing the old, damaged disc is also achieved. With previously known technology, the tooling for holding apart the vertebrae comprises an obstacle making it difficult to evacuate the old, damaged disc. This process is time consuming and positioning of a disc implant is more difficult. The integrated aspect of this invention essentially simplifies clearing out of the damaged disc, whereby the entire operation is facilitated and speeded up, resulting in a safer operation. The possibility of spanning apart, which is provided according to this aspect of the invention, makes it possible to freely remove the old disc.

The positioning of the holding means will thereby be very stable and no further engagement points, besides the ones belonging to the mechanism for spanning apart, the distance means, are necessary. The number of operation points in the patient in the form of holes for screws or the like can thereby be limited to a minimum.

The distance means preferably includes two distance means arranged in parallel each carrying the engagement means. The adjustment and handling of the holding means and the prosthesis carried thereon takes place between the parallel arranged distance means. The fixing means are suitably comprised of elongate elements, that are arranged on the distance means and are fixable thereon, which in a common crossing point are lockable, which results in a very stable fixation. The crossing point between these elements is preferably also the starting point for locking means, which, in its locked position, fixes the holding means. Preferably the locking means in the locked position also locks the fixing elements in said crossing point.

By providing the fixing elements with one slotted portion in their free regions, in the free state, sideways adjustment of the crossing point is allowed with respect to the operation point, which can be desirable for providing an accurate positioning of the prosthesis device in its rotational direction.

It is previously known to use so called retractors in the kind of surgical operation of the present type in order to hold the soft parts in the abdomen from the operation point. A system according to the invention includes and preferably carries support devices for that purpose. By fastening them to the distance means, they contribute in an optimal manner to hold the abdomen wall pressed down and the operation field free. The clearing out of the old disc is also simplified with these means.

BRIEF DESCRIPTION OF DRAWINGS

The invention will now be described by way of embodiments and with reference to the annexed drawings, wherein.

DESCRIPTION OF EMBODIMENTS

Figure 1:
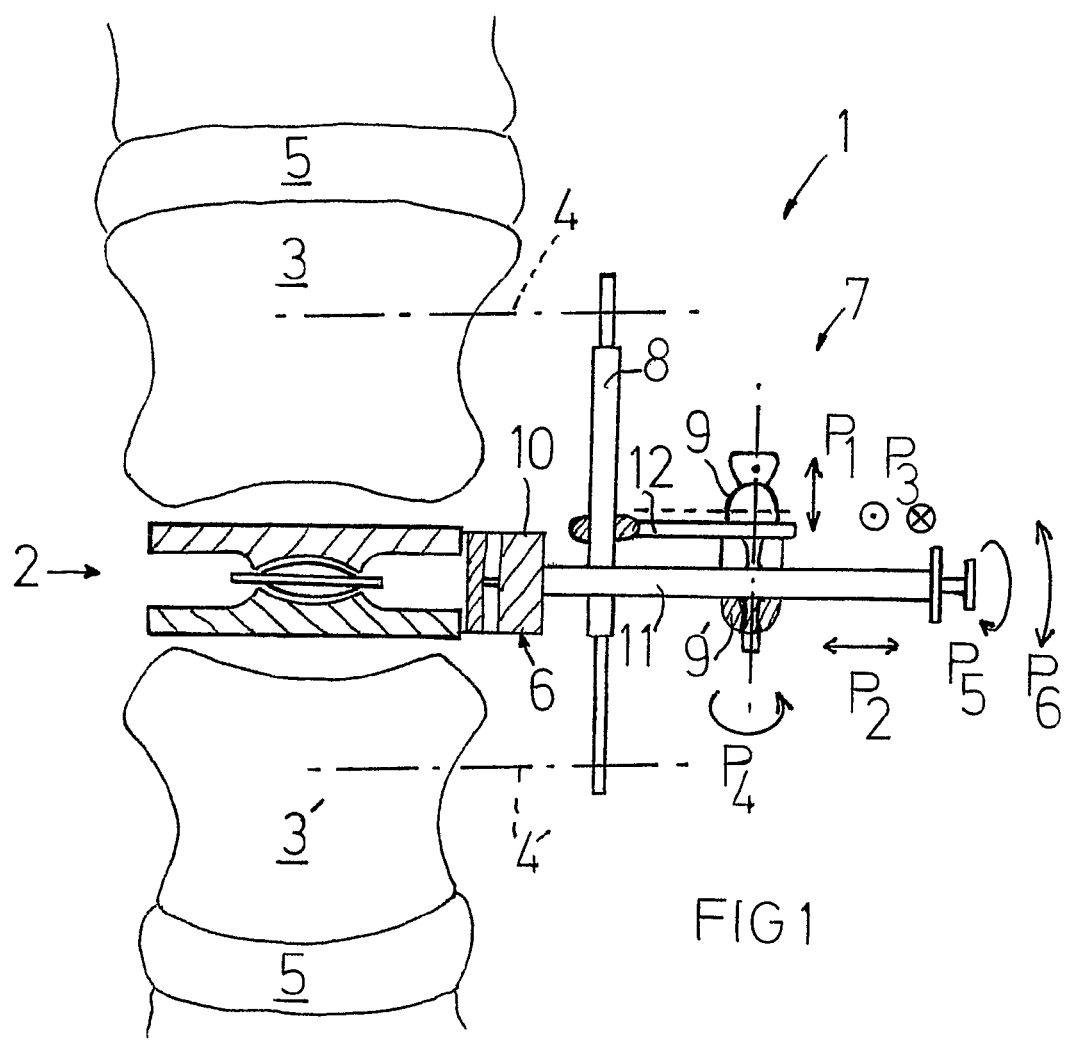
FIG. 1 shows a positioning device according to the invention during the process of introducing an implant in a spinal column, partly in section.

FIG. 1 shows a positioning device 1 in the process of positioning a disc implant 2 between two vertebrae 3 and 3' in a spinal column of a living human being. Reference numeral 5 are two healthy discs, whereas between the vertebrae 3 and 3' is cleared out all material from a damaged disc to be replaced by the disc implant 2.

The disc implant 2 is held by a holding device 6 including a fork-shaped head 10, which releasably grips around the disc implant 2 and a rod shaped manipulating element 11 which can be manipulated by hand by a surgeon. In the embodiment shown in FIG. 1, the manipulating element 11 is controlled by a fixing means 7, which in turn is connected to the distance device 8 (only one shown on FIG. 1), which in turn includes engagement means in the form of screws, (indicated with dash dotted lines, and with numerals 4 and 4'), for engagement with two vertebrae 3, 3'.

The fixing means 7 includes fixing elements 12 (only one shown in FIG. 1) together with a universal joint 9' which is lockable by means of locking means 9, wherein the universal joint 9', in a first, free state, allows adjustable movement including rotations and displacements of the holding means 6 and thereby for the disc implant 2. In a second, locked position, the locking means 9 locks the universal joint 9', and thereby the holding device 6 and the disc implant 2, in a chosen position.

As is indicated by arrows P1-P6, essentially total freedom of movement is achieved with the shown embodiment with three linear degrees of freedom P1-P3 and three rotational degrees of freedom P4-P6 for the holding device 6. It should be noted that freedom of movement in the length direction of the distance device 8 is obtained by displacement of the fixing element 12 relative thereto. Locking of the locking means 9 can suitably be arranged by means of a smaller rotation of the fixing element 12 with respect of the distance device 8 and thereby friction locking of these elements with respect of each other.

The function of the spanning device of the arrangement is such that the distance device 8 is extendable in the length direction by displacement in such a way that the engagement elements, which thus have been brought to engagement with two vertebrae because of the extension, will cause a change of the degree of separation between these vertebrae 3 and 3' with respect to each other.

This way the vertebrae can be separated and the space between them be cleared out so that the disc implant 2, without resistance, can be inserted between the vertebrae 3 and 3' and accurately positioned by the surgeon supported by simultaneous X-ray radioscopy until an optimal positioning of the disc implant 2 has been reached. Thereafter the holding device 6 is locked and thereby the prosthesis device in positioned in the chosen position with the aid of the fixing means 7, whereafter the distance device 8 is manipulated in such a way that the distance between its outer ends is reduced and the vertebrae 3 and 3' move closer to each other until they come into contact against the outer plates of the disc implant 2. Thereafter, a final control is made, by means of X-ray radioscopy or the like, that the disc implant 2 is indeed accurately positioned.

If that should not be the case, the degree of separation is again increased between the vertebrae 3 and 3' and the disc implant 2 is repositioned. When accurate positioning has been reached, the holding device 6 is removed from the disc implant 2, whereafter the distance device 8 and its engagement means 4 and 4' can be removed from the engagement with the vertebrae.

Figure 2:
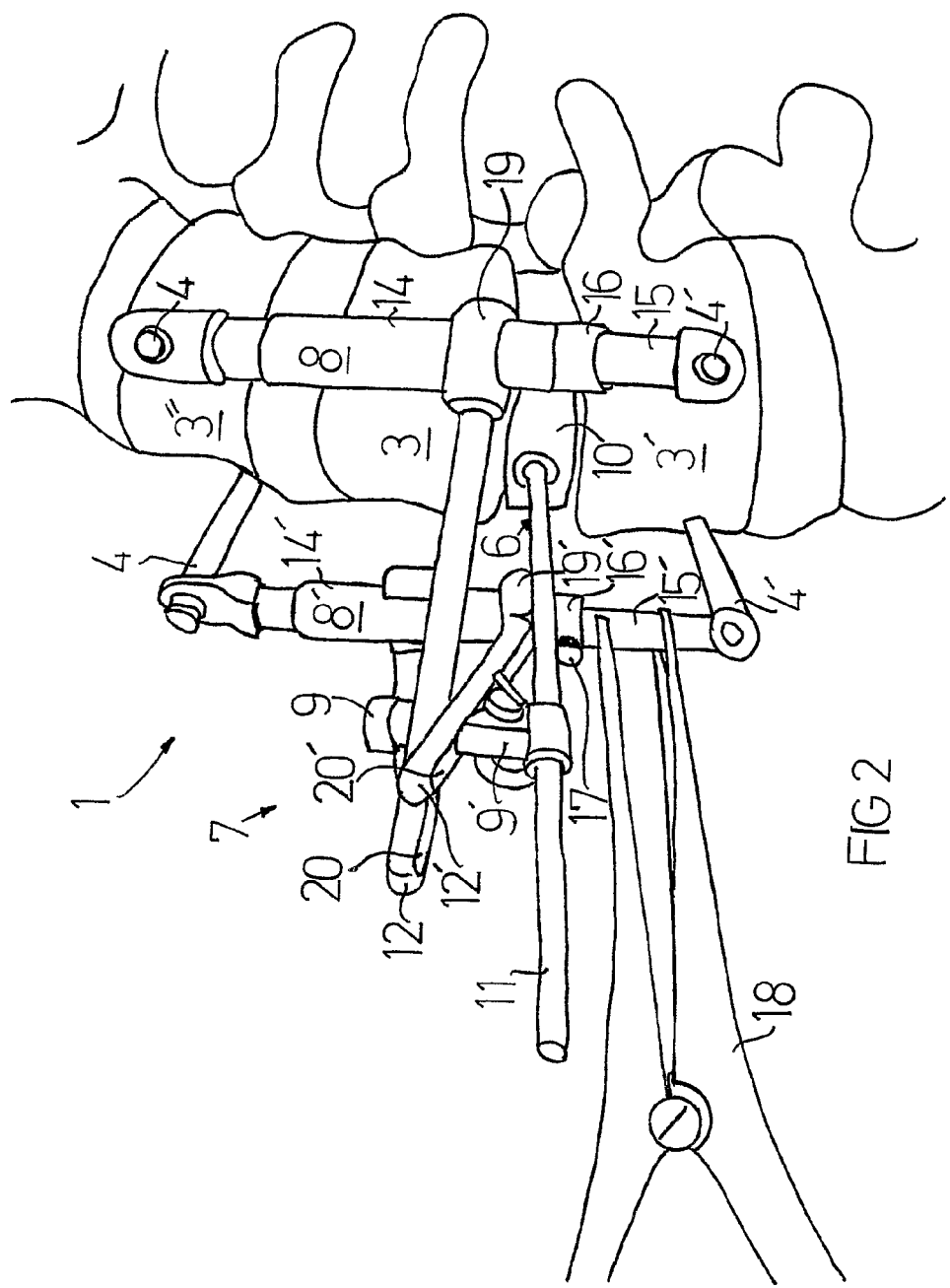
FIG. 2 shows the positioning device in FIG. 1 in a perspective view.

In FIG. 2, the positioning device 1 is represented in a perspective view in about the same position as is shown in FIG. 1. Here, it is shown that the spanning device belonging to the positioning device 1 includes two sideways separated distance means 8 and 8', which are positioned such that between them is a sufficient space for introducing a disc implant (not shown in FIG. 2), which is carried by a fork head 10 of a holding device 6.

From each one of the distance means 8 and 8', extend fixing elements 12 and 12', which are longitudinally displaceable on the respectively means 8 and 8' through sleeve portions 19. The fixing elements 12 and 12' are united at a crossing point, where locking device 9 engages. The locking device 9 also activates and deactivates a universal joint 9', which carries the manipulating element 11 of the holding device 6.

Fixing means 12 and 12' are arranged longitudinal through slots 20 and 20', in which a bolt belonging to the locking means 9 can run. This way, in a free state of the locking means, it is possible to displace the locking device and the universal joint 9' in height as well as sideways by side displacement of the locking device and the universal joint with respect to the operation point between the vertebrae 3 and 3'.

Further, the distance devices 8 and 8' are telescopic and thus axially displaceable in order to allow an increased separation of those vertebrae, with which they are in engagement. In the shown example, distance means 8 and 8' are not in engagement with two adjacent vertebrae, but with a first vertebra 3' and a second vertebra 3", whereas a third vertebra 3 is between these vertebrae. This arrangement allows better space at the place of operation.

Spanning apart the distance devices are made with a pliers device 18, which forces apart two telescopic parts 15' and 14' belonging to the distance device 8'. For fixing of an obtained separation position, a locking ring 16' is used, which locks against the smaller one of the telescopic parts 15' by means of a locking screw 17. In practice, the spanning apart of the vertebrae are made through step-wise manipulation of the pliers device 18 by first, the one on the distance devices a smaller step, locking thereof, thereafter spanning apart of the second distance device a smaller distance, locking thereof etc. etc.

Figure 3:
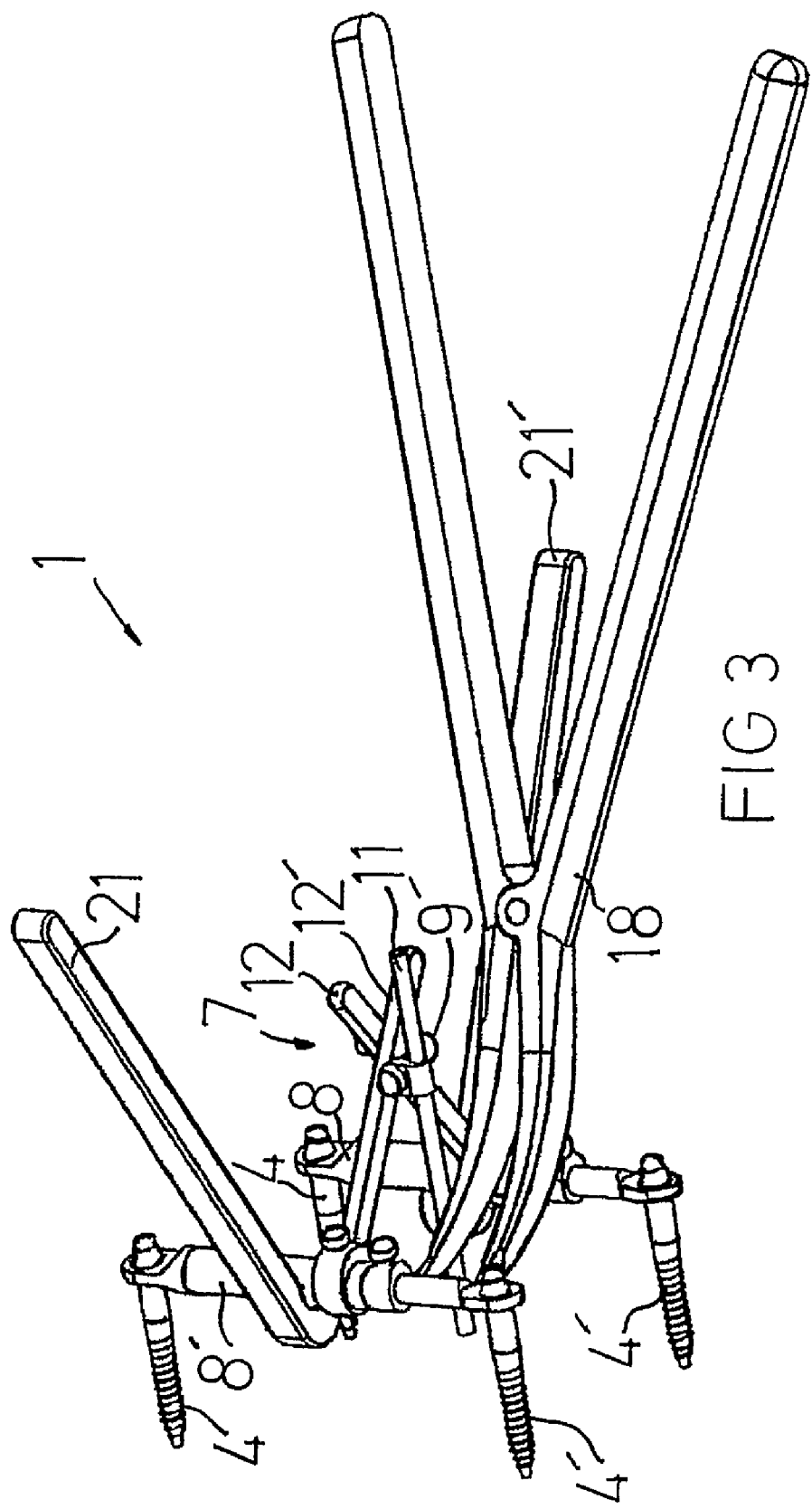
FIG. 3 shows the positioning device in FIGS. 1 and 2 in a separate perspective view.

In FIG. 3, the device of FIG. 2 is shown in a different perspective and freed from a spinal column. The distance devices 8 and 8' have at their ends known joint devices for cooperation with the engagement means 4, 4', which are comprised of known skeleton screws. By the engagement means being articulately fastened to the distance devices, excess breaking forces onto the vertebra are avoided in connection with spanning-apart the spinal column. The positioning of the screws 4, 4' in the vertebrae, which are least porous, and thereby best resist the forces for spanning apart.

On FIG. 3 also illustrates two supporting elements 21 and 21', preferably lockable and slightly curved, which are arranged for cooperation with (not shown) supporting plates for free holding the operation point from body organs in connection with the surgical operation.

Figure 4:
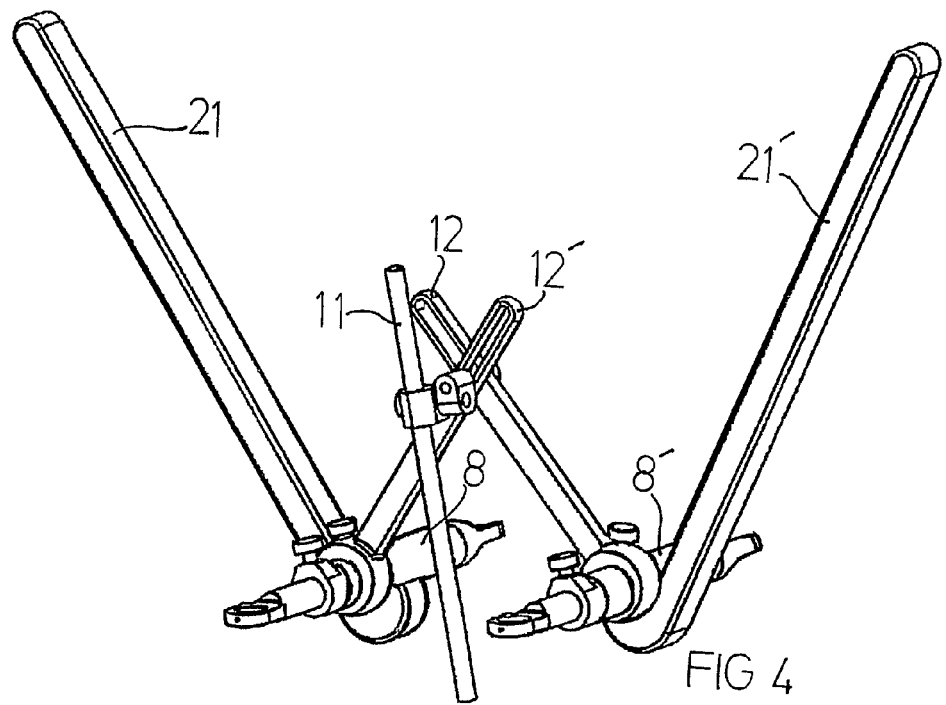
FIG. 4 shows the positioning device according to the invention with some details removed for the sake of clarity, and FIGS. 5a and b show in different views a holding device for the use with a device according to the invention.

In FIG. 4 illustrates the positioning of essential parts, according to the invention, with some details removed.

Figure 5A:
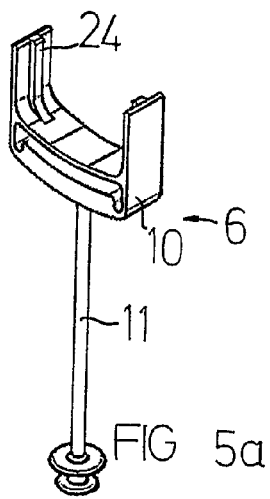
Figure 5B:
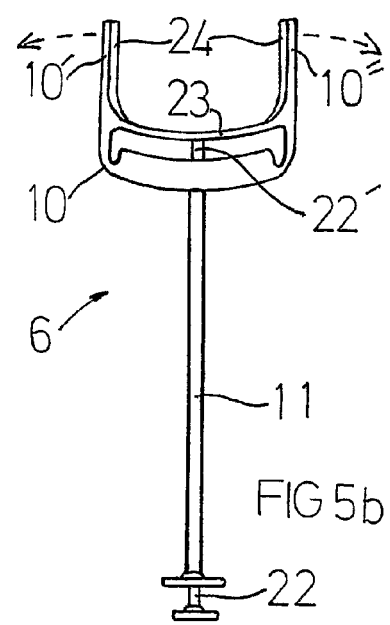

A holding device 6 is shown in FIG. 5a and b. The holding device 6 includes a fork-shaped head 10 with fork shanks 10' and 10", which form an engagement position, where, with the aid of the engagement means 24, engage a disc implant. Accordingly, holding device 6 can be brought to a position where the disc implant is released. This is achieved when the normally curved element 23 between the fork shanks 24, by means of an actuating means 22 in the form of an element inside the rod shape maneuvering element 11, is brought to a straightened state, where it presses apart the fork shanks 24. See interrupted arrows in FIG. 5b. The actuating means 22 can be manipulated by hand by a surgeon through a press button outermost on the means 22. The head 10 is preferably made of a plastic material in one piece in such a way that in an unloaded condition, it is in a position for engagement and with a bent element 23.

It should be noted that the invention can be modified within the scope of the claims. The shown embodiment with the positioning device directly cooperating with a spanning device in the form of distance means is preferred. However, it is not excluded that the positioning device is separate from the spanning device, and in that case, it is arranged such that the fixing means are fastened otherwise to one or a plurality of vertebrae. This is, however, not desired, since it means that further operations with holes etc. in the spinal column have to be made. It, however, makes it possible to use another type of spanning device for separating the vertebrae than the one that is described and shown here.

In order to arrange that a greater space is provided between two distance devices, the attachments of the engagement means can be positioned sideways outwardly, so that the distance devices can be positioned sideways with respect of the axes of the engagement means.

A modification of the spanning device can have one single distance device, which provides spanning apart instead of two that are shown in the Figures. At the ends, this single distance device can have sideward angled portions for cooperation at different positions after their lengths, with each two engagement means engaged with the vertebrae so that the spanning device includes a shallow U-shaped construction with the distance device as a web and the sideward angled portions as the shanks of the U. In this case positioning, as an example, there may need to be arranged, on the one hand, on the only distance device, and on the other hand, on a fixed point on a vertebra.

The arrangement between the distance device (devices) and the engagements means can be different: For example, an arrangement with three independent joints for allowing movements: 1: in a plane parallel with the axis of the distance device, 2: in a plane at right angle to the axis of the distance device, 3: in a plane at right angle against the axis of the engagement means (screw). Independent locking of these joints results in possibility of changing the angles of the screws, also under load, which gives greater possibilities of influencing the positions and the parallelism of the vertebrae.

The fixing means can, such other cases, be constructed otherwise, thus including portions for cooperation directly with a vertebra. Also other kinds of arrangements for locking the holding means can be envisaged. For example, with a locking device arranged at the fastening point of the fixing means on the spanning device or on the vertebra itself. It is also possible to have other types of locking and a plurality of separate locks for movements in different directions instead of the integrated lock shown in the Figures. The distance devices can be manipulated otherwise, for example, by screwing, with a notched rod with possibly a spring loaded locking device, or with a leaver mechanism.

In a simply handled modification, the distance device is maneuvered with the aid of an adjustment cable, such as a "Bowden cable", which can have its fastenings on engagement portions on mutually movable parts of a distance device in a manner which is obvious for the person skilled in the art. This way, spanning apart of two vertebrae is initiated from a distance from the area of spanning apart, which is an advantageous, since it enhances control and accessibility. Also, other arrangements, such as with a pawl and rack and corresponding actuating means with hydraulics or with pneumatics, can be used for spanning apart.

It shall be noted that it is not excluded that other prostheses are positioned with a device according to the invention, for example vertebra prostheses.

The invention claimed is:

1. A spinal prosthetic positioning device for positioning a prosthetic device in a spinal column of a living mammal, comprising:
   a prosthetic device holder for releasable connection with a prosthetic device;
   a pair of fixing elements capable of being provided in an unlocked first state where the fixing elements are capable of adjustable movement including rotation and displacement and provided in a second locked state where the holder is substantially locked in a predetermined position; and
   an elongate member affixed to the holder for connecting the fixing elements to corresponding engagement elements for engagement with said at least one vertebra, wherein:
      at least one of the engagement elements is capable of extending out in at least one direction;
      extension of the engagement elements is enabled via distance means,
      each engagement element includes at least one connecting portion for connecting the engagement element to bone, and
      a respective connecting portion is capable of extension via the distance means.

2. The device according to claim 1, further comprising a lockable universal joint which locks the pair of fixing elements in the predetermined position.

3. The device according to claim 2, wherein the lockable universal joint includes a single locking element.

4. The device according to claim 1, wherein the holder comprises a fork shaped member.

5. The device according to claim 1, wherein at least one engagement elements is capable of engagement with at least two vertebrae via the connection portions.

6. The device according to claim 1, wherein at least one of the fixing elements is adjustable relative to a corresponding engagement element.

7. The device according to claim 1, wherein the connection portion comprises an opening for receiving a fastener for fastening the engagement element to bone.

8. The device according to claim 1, wherein said distance means is selected from the group consisting of: screw means, a rack and pawl, a lever mechanism, and at least one telescopic element for achieving displacement.

9. The device according to claim 8, wherein said distance means includes at least two distance devices that are arranged substantially parallel to one another.

10. The device according to claim 9, wherein each fixing element is capable of being locked relate to a corresponding distance means.

11. The device according to claim 1, further comprising a supporting element for each of the fixing elements, wherein each supporting element cooperates with an external element for providing extension of the engagement portions.

12. A spinal prosthesis positioning device for positioning a prosthetic device in a spinal column of a living mammal, comprising:
   at least one holding means to cooperate with a prosthetic device and guide the device during positioning of the device in the spinal column;
   fixing means for fixing the positioning device with respect to at least one vertebra including connecting means for connecting the fixing means to a device for engagement with said at least one vertebra, and including at least one fixing element which is lockable on each distance device;
   locking means; and
   distance means for connecting portions for carrying engagement means at a distance from each other for engagement with two vertebrae, said distance means including at least two distance devices arranged substantially parallel to one another for carrying vertebral engagement means, and said distance means includes displacement means allowing displacement of said connecting portions with respect to each other when the engagement means are engaged with said vertebrae in order to alter the degree of separation of said vertebrae,
   wherein upon said locking means being in a first, free state, adjustment of said holding means is allowed, and wherein upon said locking means being in a second, locked state, said holding means is fixed in a selected position.

13. The device according to claim 12, wherein said fixing means includes two fixing elements each initially positioned in a different engagement position, and wherein said fixing elements are mutually lockable using said locking means.

14. The device according to claim 12, further comprising a universal joint which is lockable and releasable using said locking means.

15. The positioning device according to claim 12, wherein said locking means is lockable using one single locking element.

16. The positioning device according to claim 12, wherein said fixing means are adjustable and fixable on said distance means.

17. The positioning device according to claim 12, wherein said distance means is selected from the group comprising: screw means, rack and pawl, lever mechanism, telescopic elements for achieving displacement of the connecting portions.

18. The positioning device according to claim 12, wherein said distance means includes mutually displaceable portions for allowing displacement of the connecting portions.

19. The positioning device according to claim 18, wherein the mutually displaceable portions are telescopic.

20. The positioning device according to claim 18, wherein the mutually displaceable portions are lockable with respect to each other.

21. The positioning device according to claim 18, wherein the mutually displaceable portions include cooperation means for cooperating with an external means for providing a mutual displacement of the portions.

22. The positioning device according to claim 12, wherein said connection portions include joint means for allowing articulating movements of the engagement means with a respect to said distance means.

* * * * *